(12) United States Patent
Patzke

(10) Patent No.: US 10,488,308 B2
(45) Date of Patent: Nov. 26, 2019

(54) PREPARATION OF LIPEMIC PLASMA OR SERUM SAMPLES FOR THE DETERMINATION OF A LIPID INTERFERENCE

(71) Applicant: Siemens Healthcare Diagnostics Products GmbH, Marburg (DE)

(72) Inventor: Juergen Patzke, Marburg (DE)

(73) Assignee: Siemens Healthcare Diagnostics Products GmbH

( * ) Notice: Subject to any disclaimer, the term of this patent is extended or adjusted under 35 U.S.C. 154(b) by 225 days.

(21) Appl. No.: 15/698,618

(22) Filed: Sep. 7, 2017

(65) Prior Publication Data

US 2018/0067022 A1 Mar. 8, 2018

(30) Foreign Application Priority Data

Sep. 8, 2016 (EP) .................................... 16187839

(51) Int. Cl.
*G01N 1/40* (2006.01)
*G01N 33/92* (2006.01)

(52) U.S. Cl.
CPC ........... *G01N 1/4077* (2013.01); *G01N 33/92* (2013.01); *G01N 2001/4083* (2013.01); *G01N 2800/044* (2013.01)

(58) Field of Classification Search
None
See application file for complete search history.

(56) References Cited

PUBLICATIONS

Akbas et al. Annals of Clinical & Laboratory Science 2015, vol. 45, p. 562-5640 (Year: 2015).*
Sun Diagnostics Jun. 27, 2014 "Is Intralipid adequate for Interference Testing?" (Year: 2014).*
Grunbaum et al. Clinical Toxicology 2016 vol. 54, p. 92-102 (Year: 2016).*
Christian Heller et al.; "Lipid Interference in the Determination of the Concentration of Haemoglobin in Plasma Using the ACA SX Analyzer"; Eur J Clin Chem Clin Biochem 1996; Walter de Gruyter: Berlin, New York; vol. 34; pp. 811-816.
Bornhorst, J.A. et al, Assay-specific differences in lipemic interference in native and Intralipid-supplemented samples. Clin. Chem. 2004, 50(11): 2197-2201.; 2004.
European Search Report of European Application No. EP16187839. 2—1405, dated Feb. 28, 2017.

* cited by examiner

*Primary Examiner* — Changhwa J Cheu
(74) *Attorney, Agent, or Firm* — Dugan & Dugan, PC

(57) ABSTRACT

The present invention is in the field of in vitro diagnostics and relates to a method for preparing lipemic plasma or serum samples and the use thereof for establishing a lipid interference in the quantitative determination of the amount or the activity of an analyte in a plasma or serum sample.

9 Claims, 2 Drawing Sheets

PREPARATION OF LIPEMIC PLASMA OR SERUM SAMPLES FOR THE DETERMINATION OF A LIPID INTERFERENCE

CROSS REFERENCE TO RELATED APPLICATION

This claims priority to European Patent Application No. EP 16187839.2, filed Sep. 8, 2016, which is hereby incorporated by reference herein in its entirety for all purposes.

FIELD

The present invention is in the field of in vitro diagnostics and relates to a method for preparing lipemic plasma or serum samples and the use thereof for establishing a lipid interference in the quantitative determination of the amount or the activity of an analyte in a plasma or serum sample.

BACKGROUND

The determination of clinically relevant parameters in plasma and serum samples can be significantly influenced by elevated triglyceride concentrations (lipemia). Lipemic samples with elevated triglyceride concentration occur relatively frequently and can, for example, be caused by a high-fat diet, diabetes mellitus, chronic kidney failure, pancreatitis, lupus erythematosus, multiple myeloma, or the intake of medicaments or oral contraceptives.

The interfering effect of elevated triglyceride concentrations is primarily based on the clouding (turbidity) of the samples, which is sometimes visible to the naked eye and which results in an increased light scattering and absorption. This phenomenon interferes with photometric assay systems most of all. A further interfering effect is that the solubility of an analyte to be detected can be impaired.

Therefore, modern automatic analyzers increasingly comprise so-called preanalytical analysis units, in which the sample material is analyzed with respect to any interference substances, such as lipids, hemoglobin and bilirubin, before the actual determination of one or more specific analytes is carried out. If critical amounts of one or more interference substances are established in a sample, it is, for example, possible to provide the assay results obtained for the sample with a warning, meaning that a user is informed that a false result has possibly been measured here.

Since the triglyceride concentration which causes a significant interference is different for each assay and depends on the analyzer used, the regents used, etc., it is necessary to carry out interference studies for each assay in order to ascertain from which triglyceride concentration a specific assay no longer provides reliable assay results.

A problem is that there is as yet no standardized lipemic sample material, which is required for carrying out the interference studies. To date, Intralipid, a soybean lipid emulsion, is frequently added to human plasma samples or plasma pools in order to simulate lipemic interferences. However, it has been found that the addition of Intralipid is not a generally applicable method of lipid-interference determination, because the interferences caused by Intralipid do not correlate in all cases with the interferences occurring in native lipemic samples (Bornhorst, J. A. et al., Assay-specific differences in lipemic interference in native and Intralipid-supplemented samples. Clin. Chem. 2004, 50(11): 2197-2201). Therefore, it is preferred to use lipemic donor samples for interference studies.

However, sufficient amounts of native lipemic patient samples, particularly those with exceptionally high triglyceride concentrations (>500 mg/dL), are only obtainable with a very high degree of effort, since extremely large donor groups would have to be examined.

SUMMARY

It is therefore an object of the present invention to find a simpler method for providing lipemic plasma or serum samples.

The object is achieved according to the invention by centrifuging a lipid-containing plasma or serum sample in order to obtain a lipid-enriched phase and then adding the lipid-enriched phase to a plasma or serum sample.

This has the advantage that any desired triglyceride concentration can be generated without artificial substances such as Intralipid having to be used.

The present invention thus provides a method for preparing a lipemic plasma or serum sample. The method comprises the following steps:

(a) centrifuging a lipid-containing plasma or serum sample in order to separate a lipid-containing supernatant from a lipid-depleted phase;

(b) removing the lipid-containing supernatant and (c) mixing the lipid-containing supernatant with a plasma or serum sample.

The terms "triglyceride(s)" and "lipid(s)" are used synonymously.

The term "lipemic plasma or serum sample" is to be understood to mean a plasma or serum sample from an individual donor or a mixture (pool) of plasma or serum samples from multiple donors, the triglyceride concentration of which is above the reference range, i.e., which is 150 mg/dL (1.71 mmol/L) or more.

The term "lipid-containing plasma or serum sample" is to be understood to mean a plasma or serum sample from an individual donor or a mixture (pool) of plasma or serum samples from multiple donors, the triglyceride concentration of which is within or above the reference range of 150 mg/dL (1.71 mmol/L).

The invention is based particularly on human plasma and serum samples. However, an analogous approach is in principle also applicable for animal plasma and serum samples.

In a preferred embodiment, a lipid-containing plasma or serum sample is divided, and a first subamount of the lipid-containing plasma or serum sample is centrifuged in step (a) of the method and the lipid-containing supernatant is then removed in step (b), and the lipid-containing supernatant is then mixed with a second subamount of the same lipid-containing plasma or serum sample in step (c). This has the advantage that, in this specific sample having, for example, a defined analyte concentration or activity, only the lipid fraction is increased, whereas the remaining sample composition remains unchanged. Furthermore, it is advantageous that the interference caused by the lipid of this specific sample can be examined. Thus, it would be possible in a study with multiple different lipemic samples to also include the variability of said samples with respect to the interference in the final determination of the interference limit.

Alternatively, the removed lipid-containing supernatant can be mixed in step (c) with a subamount of the lipid-depleted phase of the centrifuged sample.

The mixing ratio of lipid-containing supernatant and plasma or serum sample self-evidently depends on the triglyceride concentration of the starting materials and the desired triglyceride concentration.

The centrifugation of the lipid-containing plasma or serum sample in step (a) is preferably done for at least 10 minutes at at least 2000×g. The use of longer centrifugation times and higher centrifugal forces is definitely possible, such as, for example, for 10 minutes at 15 000×g or for 60 minutes at 82 000×g or else for 60 minutes at 133 000×g.

The centrifugation of a lipid-containing plasma or serum sample leads to the separation of a cloudy, lipid-containing supernatant from an underlying clear lipid-depleted phase, which separation is visible to the naked eye. The removal of the lipid-containing supernatant can, for example, be achieved by carefully piercing through the lipid-containing supernatant using a pipette needle and carefully sucking off the lipid-depleted phase, meaning that only the lipid-containing supernatant remains in the vessel. As a result of addition of a plasma or serum sample to the vessel and shaking, the sample is mixed with the lipid-containing supernatant. Other known homogenization methods, such as, for example, an ultrasound treatment, can also be used.

The present invention further provides for the use of a lipemic plasma or serum sample prepared using a method according to the invention in a method for establishing a lipid interference in a method for quantitatively determining the amount or the activity of an analyte in a plasma or serum sample.

Preferably, a lipemic plasma or serum sample prepared according to the invention is used in a method for establishing a lipid interference in a method for quantitatively determining the amount or the activity of an analyte in a plasma or serum sample, wherein the method for establishing a lipid interference comprises the following steps:

(a) providing a first assay mix by mixing at least one analyte-specific detection reagent with a nonlipemic plasma or serum sample having an analyte concentration or activity and measuring a first assay result;

(b) providing a second assay mix by mixing the same at least one analyte-specific detection reagent with a lipemic plasma or serum sample having the same analyte concentration or activity and measuring a second assay result;

(c) establishing a difference between the first and second assay result; and (d) establishing a lipid interference when the difference between the first and second assay result exceeds a predetermined tolerance limit, for example when the difference between the first and second assay result is 5% or more.

In this way, it is possible to determine for each analytical assay from which triglyceride concentration the assay no longer provides reliable assay results.

An "analyte" is to be understood to mean a substance to be detected in a sample material (in this case, plasma or serum) or a measurable property of the sample material, which property is influenced by a plurality of substances. An analyte can, for example, be a peptide, a protein, a polysaccharide or a nucleic acid, particularly a protein or protein complex having a particular biological function, such as, for example, immunoglobulins, cytokines, receptors, enzymes, hormones, cancer antigens, tissue-specific antigens, blood coagulation factors, antigens from microbial pathogens, etc. A typical plasma-sample property influenced by a plurality of substances is, for example, coagulation time. Coagulation assays allow the measurement of the activity of an individual or of multiple coagulation factors by means of the measurement of the rate of fibrin formation in vitro.

The method for quantitatively determining the amount or the activity of an analyte in a plasma or serum sample can be any conceivable assay principle, such as, for example, a particle-enhanced immunoassay, a chromogenic assay or a coagulation assay.

An analyte-specific detection reagent contains one or more substances which allow the detection of a specific analyte or of another measurable property of the sample, for example one or more antibodies or antigens, chromogenic peptide substrates and/or enzyme activators. It can, for example, be envisaged to mix a liquid detection reagent containing the analyte-specific substances in dissolved form with the sample. Alternatively, it can be envisaged that a detection reagent consists of a solid phase coated with one or more analyte-specific substances.

Depending on the assay principle used, the measurement of the assay results can be done, for example, spectrophotometrically, turbidimetrically, nephelometrically, luminometrically, fluorometrically, radiometrically, etc.

To establish a lipid interference, i.e., a significant impairment of the measurement accuracy of an assay method, the same assay method is carried out both with a nonlipemic plasma or serum sample (having a triglyceride concentration of ≤150 mg/dL) as reference sample and with at least one lipemic plasma or serum sample prepared according to the invention (having a triglyceride concentration of >150 mg/dL). If the two samples have the same analyte concentration or activity, a difference between the first and second assay result can be attributed to the elevated triglyceride concentration of the lipemic sample. Preferably, the reference sample is the lipid-depleted phase of the lipid-containing sample which was centrifuged for the preparation of the lipemic sample.

There is a lipid interference when the difference between the first and second assay result exceeds a predetermined tolerance limit, for example when the relative difference between the first and second assay result is 5% or more. It is also possible to define a maximal absolute analyte difference as tolerance limit.

Preferably, multiple samples, preferably 10 to 20, are measured for a lipid interference study for each sample type, making it possible to carry out a statistical evaluation. Preferably, 10 to 20 nonlipemic samples of normal analyte concentration or activity and the same number of lipemic samples of normal analyte concentration or activity are measured. Additionally or alternatively, a number of nonlipemic samples and, in parallel, the same number of lipemic samples having analyte concentrations or activities covering the measurement range of the assay method can be measured. Furthermore, it is also possible to measure different lipemic sample types of normal, reduced or elevated analyte concentration or activity, which sample types have different triglyceride concentrations above the reference range, i.e., concentrations between 150 and 3000 mg/dL.

Preferably, a lipemic plasma or serum sample and a nonlipemic plasma or serum sample which have been prepared from the same lipid-containing plasma or serum sample as starting material are used to establish a lipid interference. This has the advantage that the sample composition and thus also the analyte concentration is identical in the two samples, apart from the lipid fraction, the influence of which is to be examined.

Further preferably, the nonlipemic plasma or serum sample can have been prepared using a method comprising the following steps:

(a) centrifuging a lipid-containing plasma or serum sample and isolating the lipid-depleted phase from the lipid-containing supernatant.

This has the advantage that it is possible to use the lipid-depleted phase arising as by-product in the preparation of the lipid-containing supernatant intended for the preparation of a lipemic sample, making it possible to use an existing starting material with the minimum of waste.

A lipemic plasma or serum sample prepared according to the invention can also be used in a method for establishing a lipid interference in a method for quantitatively determining the amount or the activity of an analyte in a plasma or serum sample, wherein the method for establishing a lipid interference comprises the following steps:

(a) providing a first assay mix by mixing at least one analyte-specific detection reagent with a first subamount of a nonlipemic plasma or serum sample and measuring a first assay result;

(b) providing a second assay mix by mixing the same at least one analyte-specific detection reagent with the lipid-depleted phase of a second subamount of the same nonlipemic plasma or serum sample, which had previously been centrifuged at at least 2000 g for at least 10 minutes, and measuring a second assay result; and (c) establishing a first difference between the first and second assay result; and (d) providing a third assay mix by mixing the same at least one analyte-specific detection reagent with a first subamount of a lipemic plasma or serum sample and measuring a third assay result;

(e) providing a fourth assay mix by mixing the same at least one analyte-specific detection reagent with the lipid-depleted phase of a second subamount of the same lipemic plasma or serum sample, which had previously been centrifuged at at least 2000 g for at least 10 minutes, and measuring a fourth assay result; and (f) establishing a second difference between the third and fourth assay result; and (g) establishing a lipid interference when the deviation between the first and second difference exceeds a predetermined tolerance limit, for example when the deviation between the first and second difference, which are, for example, expressed as relative differences in each case, exceeds 5% or more.

A lipemic plasma or serum sample prepared according to the invention can also be used in one embodiment of the method for establishing a lipid interference in a method for quantitatively determining the amount or the activity of an analyte in a plasma or serum sample, wherein the embodiment of the method for establishing a lipid interference comprises the following steps:

(a) providing multiple first assay mixes by, in each case, mixing at least one analyte-specific detection reagent with, in each case, a first subamount of nonlipemic plasma or serum samples and measuring multiple first assay results;

(b) providing multiple second assay mixes by, in each case, mixing the same at least one analyte-specific detection reagent with, in each case, the lipid-depleted phase of a second subamount of the same nonlipemic plasma or serum samples, which had previously been centrifuged at at least 2000 g for at least 10 minutes, and measuring multiple second assay results; and (c) establishing a first difference between the particular first and second assay result and calculating a mean of all established first differences; and (d) providing a third assay mix by mixing the same at least one analyte-specific detection reagent with a first subamount of a lipemic plasma or serum sample and measuring a third assay result;

(e) providing a fourth assay mix by mixing the same at least one analyte-specific detection reagent with the lipid-depleted phase of a second subamount of the same lipemic plasma or serum sample, which had previously been centrifuged at at least 2000 g for at least 10 minutes, and measuring a fourth assay result; and (f) establishing a second difference between the third and fourth assay result; and (g) calculating a corrected second difference by subtracting the mean of all established first differences; and (h) establishing a lipid interference when the corrected second difference exceeds a predetermined tolerance limit, for example when the corrected difference exceeds a previously determined confidence interval of 10%.

This has the advantage that it is possible to identify any effects of the centrifugation method used to prepare the lipid-depleted phase of a sample, which effects may alter the analyte concentration. If the centrifugation method itself alters the analyte level of the sample, this effect must be taken into account when ascertaining an interference. For example, it is conceivable in the case of a coagulation assay that important vesicle-bound factors are sedimented owing to the centrifugation and this alone causes the coagulation time to change. For this reason, the centrifugation method is used not only for lipemic samples, but also for nonlipemic samples. If, for example, both in the case of lipemic samples and in the case of nonlipemic samples, a deviation of the analyte level of, relatively, 10% in the lipid-depleted phase with respect to the noncentrifuged sample is established in each case, this can be attributed to the centrifugation. There is then no triglyceride interference. If the centrifugation method generates a deviation of +10% in the analyte level of nonlipemic samples and a deviation of +20% is observed in lipemic samples, it is possible to infer therefrom a 10% interference due to the triglycerides.

Since both the extent of the interference and the possible influence of the centrifugation method may vary greatly in individual nonlipemic and lipemic samples, it is useful to measure lipemic samples having different triglyceride levels and different analyte levels and nonlipemic samples having different analyte levels.

DETAILED DESCRIPTION

Figure 1:
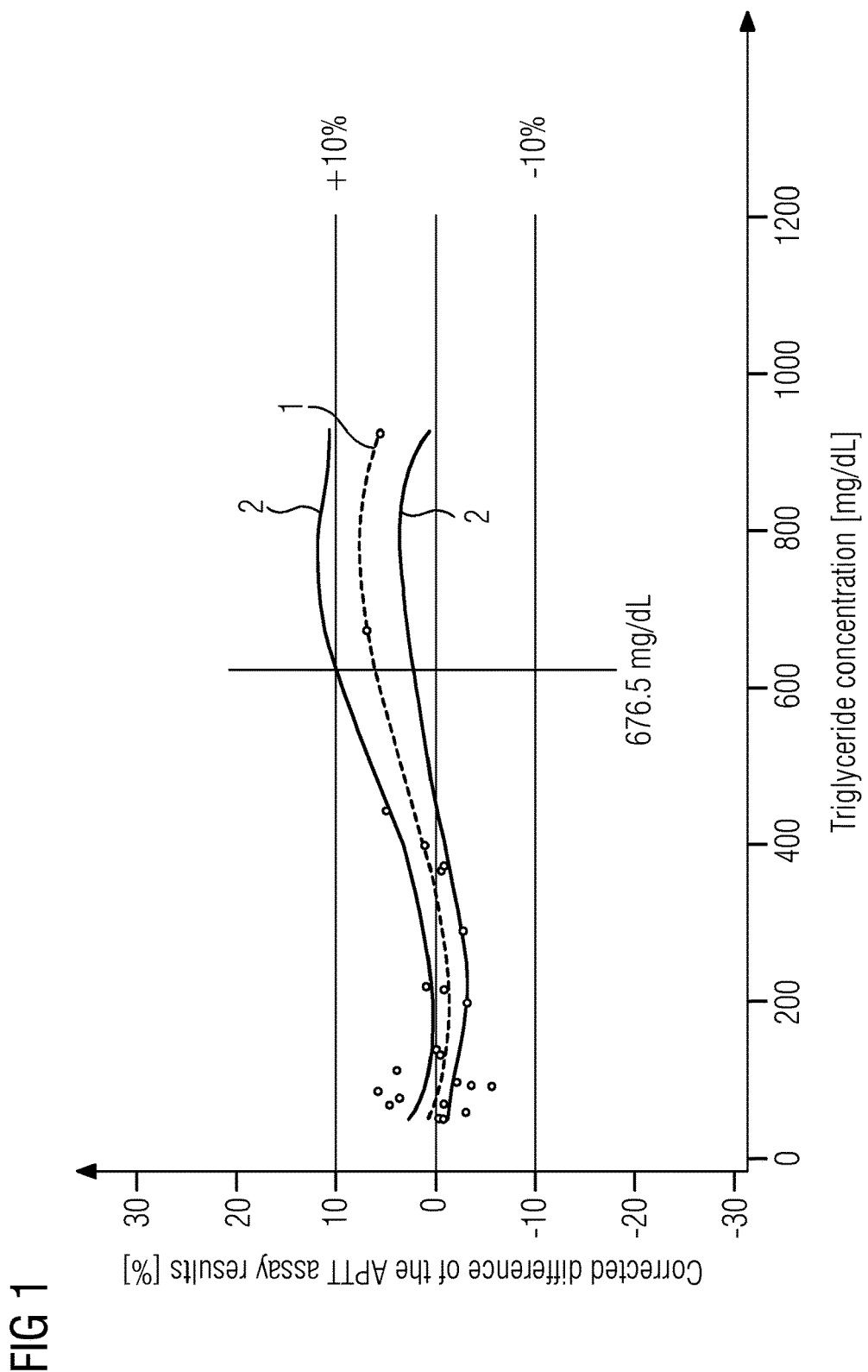
FIG. 1—Determination of the lipid interference in a method for determining the APTT.

The following exemplary embodiments serve to illustrate the method according to the invention and are not to be understood as a restriction.

EXAMPLES

Example 1

Determination of the Lipid Interference in a Method for Determining the APTT

1a) Inventive Preparation of Lipemic Plasma Samples for the Determination of the Lipid Interference in a Method for Determining the APTT Using Dade Actin Reagent Use was made of 7 native lipemic citrate plasma samples (triglyceride level >150 mg/dL) from 7 donors. The triglyceride level was determined using the TRIG assay and using the Dimension Vista System (Siemens Healthcare, Newark, USA). About 18 to 20 mL of said samples were centrifuged for 1 hour in an ultracentrifuge (Thermo Scientific Sorval WX Ultra, Rotor T-1250, ThermoFisher, Hanau, Germany) at 33 200 rpm, corresponding to 133 000×g. With the aid of a pipette, the uppermost, lipid-rich supernatant was carefully removed while avoiding mixing with the underlying lipid-depleted phase. Depending on the sample, between 0.7 and 3.0 mL of said lipid-rich supernatant were mixed with a noncentrifuged subamount of the native citrate plasma sample from the same donor and, in some cases, with a nonlipemic factor deficiency plasma (triglyceride level typically approx. 100 mg/dL). The total volume of the thus prepared lipemic samples was about 12 mL. The triglyceride level of the thus prepared samples was measured again and was between 234 mg/dL and 1007 mg/dL.

Table 1 contains the final triglyceride concentration of the lipemic sample Nos. L3-L9 prepared according to the invention and three further native lipemic samples (sample Nos. L1, L2 and L10) and also the mixing ratio of the amount of native (noncentrifuged, untreated) plasma sample from the donor, lipid-containing supernatant, deficiency plasma and a heparin solution. The mixing with deficiency plasma or heparin solution was done to expand the APTT measurement range.

Table 2 contains the composition and the final triglyceride concentration of the nonlipemic sample Nos. NL1-NL12, which were likewise used in the interference study.

TABLE 1

Composition Of The Lipemic Samples

| Sample No. | Native sample amount mL | Lipid-containing supernatant mL | Plasma with a deficiency of | | | Heparin solution mL | Final triglyceride concentration mg/dL |
|---|---|---|---|---|---|---|---|
| | | | FV mL | FVII mL | PC mL | | |
| L1 | 12.0 | 0.0 | 0.0 | 0.0 | 0.0 | 0.0 | 237.5 |
| L2 | 12.0 | 0.0 | 0.0 | 0.0 | 0.0 | 0.0 | 399.5 |
| L3 | 11.1 | 0.9 | 0.0 | 0.0 | 0.0 | 0.0 | 731.0 |
| L4 | 3.0 | 3.0 | 0.0 | 6.0 | 0.0 | 0.0 | 316.5 |
| L5 | 3.0 | 2.5 | 0.0 | 0.0 | 8.0 | 0.0 | 481.5 |
| L6 | 6.5 | 0.7 | 0.0 | 5.0 | 0.0 | 0.0 | 1006.6 |
| L7 | 3.5 | 1.2 | 7.5 | 0.0 | 0.0 | 0.0 | 233.5 |
| L8 | 4.0 | 2.0 | 6.0 | 0.0 | 0.0 | 0.0 | 405.5 |
| L9 | 4.5 | 1.6 | 6.0 | 0.0 | 0.0 | 0.0 | 432.5 |
| L10 | 12.0 | 0.0 | 0.0 | 0.0 | 0.0 | 0.5 | 215.5 |

TABLE 2

Composition Of The Nonlipemic Samples

| Sample No. | Native sample amount mL | Lipid-containing supernatant mL | Plasma with a deficiency of | | | Heparin solution mL | Final triglyceride concentration mg/dL |
|---|---|---|---|---|---|---|---|
| | | | FV mL | FVII mL | PC mL | | |
| NL1 | 12.0 | — | 0.0 | 0.0 | 0.0 | 0.0 | 148.0 |
| NL2 | 12.0 | — | 0.0 | 0.0 | 0.0 | 0.0 | 120.5 |
| NL3 | 12.0 | — | 0.0 | 0.0 | 0.0 | 0.0 | 73.5 |
| NL4 | 12.0 | — | 0.0 | 0.0 | 0.0 | 0.0 | 52.6 |
| NL5 | 6.0 | — | 6.0 | 0.0 | 0.0 | 0.0 | 143.5 |
| NL6 | 12.0 | — | 0.0 | 0.0 | 0.0 | 0.0 | 83.0 |
| NL7 | 1.2 | — | 0.0 | 10.8 | 0.0 | 0.0 | 100.0 |
| NL8 | 3.0 | — | 0.0 | 9.0 | 0.0 | 0.0 | 99.5 |
| NL9 | 7.0 | — | 5.0 | 0.0 | 0.0 | 0.0 | 62.5 |
| NL10 | 6.0 | — | 6.0 | 0.0 | 0.0 | 0.0 | 105.5 |
| NL11 | 6.6 | — | 5.4 | 0.0 | 0.0 | 0.0 | 107.0 |
| NL12 | 12.0 | — | 0.0 | 0.0 | 0.0 | 0.2 | 92.2 |
| NL13 | 11.5 | — | 0.0 | 0.0 | 0.0 | 0.6 | 53.8 |
| NL14 | 12.0 | — | 0.0 | 0.0 | 0.0 | 0.7 | 73.8 |

1b) Determination of the Lipid Interference in a Method for Determining the APTT Using Dade Actin Reagent In the case of the activated partial thromboplastin time (APTT), a plasma sample is mixed with reagents containing phospholipids and a surface activator (Dade Actin reagent, Siemens Healthcare, Marburg, Germany). After an incubation time, coagulation is initiated by the addition of $CaCl_2$. In the example described here, the APTT was automatically processed on the Sysmex CS-5100 analyzer (Siemens Healthcare, Marburg, Germany). The coagulation reaction is measured photometrically as an increase in absorbance. The time until a particular increase in absorbance is the coagulation time in seconds, which represents the result of the APTT assay.

From all of the samples prepared under 1a), a subamount was used for the measurement of the APTT (assay result 1). A second subamount of each of the samples prepared under 1a) was centrifuged at 133 000×g for 1 hour and the lipid-depleted phase was used as sample for the APTT measurement (assay result 2). If the centrifugation has no influence, the lipid-depleted phase of the centrifuged aliquot should contain the same analyte amount as the noncentrifuged sample. The two assay results (coagulation times in seconds) of each sample were compared with one another, and the relative difference in % was calculated: 100×(assay result 1-assay result 2)/assay result 2.

From the relative differences of the assay results for the nonlipemic samples, the mean was calculated (in this case: 0.6). Since the nonlipemic samples exhibit no interference due to lipemia, this mean difference is attributed to a nonspecific influence factor of the method (e.g., the centrifugation). For the correction of this effect, a corrected difference was ascertained for each sample by subtracting said mean from the relative difference. The corrected difference is a measure of the interference caused by lipids.

Table 3 shows for each sample the assay results 1 and 2, the ascertained relative difference and the corrected difference. The difference values are rounded values.

TABLE 3

APTT Assay Results And Deviations

| Sample No. | | Triglyceride concentration mg/dL | Noncentrifuged subamount of the sample 1st assay result APTT [s] | Lipid-depleted phase of a centrifuged subamount of the sample 2nd assay result APTT [s] | Relative difference % | Corrected difference % |
|---|---|---|---|---|---|---|
| NL1 | Nonlipemic | 148.0 | 26.4 | 26.2 | 0.6 | −0.0 |
| NL2 | | 120.5 | 27.8 | 26.6 | 4.5 | 3.9 |
| NL3 | | 73.5 | 28.5 | 27.1 | 5.2 | 4.6 |
| NL4 | | 52.6 | 23.0 | 23.1 | −0.2 | −0.8 |
| NL5 | | 143.5 | 34.6 | 34.5 | 0.3 | −0.3 |
| NL6 | | 83.0 | 32.7 | 31.4 | 4.3 | 3.7 |
| NL7 | | 100.0 | 30.1 | 31.0 | −2.9 | −3.5 |
| NL8 | | 99.5 | 28.4 | 29.9 | −5.0 | −5.6 |
| NL9 | | 62.5 | 39.8 | 40.8 | −2.3 | −2.9 |
| NL10 | | 105.5 | 38.2 | 38.8 | −1.5 | −2.1 |
| NL11 | | 107.0 | 37.6 | 38.1 | −1.3 | −1.9 |
| NL12 | | 92.2 | 65.0 | 61.1 | 6.5 | 5.9 |
| NL13 | | 53.8 | 115.8 | 115.5 | 0.3 | −0.3 |
| NL14 | | 73.8 | 100.1 | 100.3 | −0.2 | −0.8 |
| | | | | Mean: | 0.6 | |
| L1 | Lipemic | 237.5 | 27.1 | 26.7 | 1.5 | 0.9 |
| L2 | | 399.5 | 22.8 | 22.8 | 0.0 | −0.6 |
| L3 | | 731.0 | 22.2 | 20.7 | 7.5 | 6.9 |
| L4 | | 316.5 | 28.7 | 29.4 | −2.2 | −2.8 |
| L5 | | 481.5 | 30.6 | 29.0 | 5.5 | 4.9 |
| L6 | | 1006.6 | 25.2 | 23.8 | 6.1 | 5.5 |
| L7 | | 233.5 | 42.0 | 42.1 | −0.2 | −0.8 |
| L8 | | 405.5 | 36.2 | 36.3 | −0.3 | −0.9 |
| L9 | | 432.5 | 40.7 | 40.0 | 1.6 | 1.0 |
| L10 | | 215.5 | 68.9 | 70.6 | −2.5 | −3.1 |

The corrected difference, i.e., the deviation of the assay results of the noncentrifuged samples from the assay results of the centrifuged samples (decreased by the mean of the difference of the nonlipemic samples), was plotted against the triglyceride concentration of the noncentrifuged samples (FIG. 1, line 1). A polynomial fitting method was applied and the associated confidence interval calculated (FIG. 1, lines 2). The point of intersection of the limit of the confidence interval with the criterion of 10% relative deviation identifies the triglyceride concentration from which a lipid interference is to be expected in the tested APTT assay method (676.5 mg/dL).

Example 2

Determination of the Lipid Interference in a Method for Determining Protein C

2a) Inventive Preparation of Lipemic Plasma Samples for the Determination of the Lipid Interference in a Method Fort Determining Protein C Using the Berichrom Protein C Assay Use was made of 12 native lipemic citrate plasma samples (triglyceride level >150 mg/dL) from 12 donors, and the procedure as described under 1a) was carried out. The triglyceride level of the thus prepared samples was measured again and was between 199 mg/dL and 1007 mg/dL.

Table 4 contains the final triglyceride concentration of the lipemic sample Nos. L1-L12 prepared according to the invention and of a further native lipemic sample (sample No. L13) and also the mixing ratio of the amount of native (noncentrifuged, untreated) plasma sample from the donor, lipid-containing supernatant, deficiency plasma and a heparin solution. The mixing with deficiency plasma was done to expand the protein C measurement range.

Table 5 contains the composition and the final triglyceride concentration of the nonlipemic sample Nos. NL1-NL12, which were likewise used in the interference study.

TABLE 4

Composition Of The Lipemic Samples

| | Composition | | | | | | |
|---|---|---|---|---|---|---|---|
| | Native sample | Lipid-containing | Plasma with a deficiency of | | | Heparin | Final triglyceride |
| Sample No. | amount mL | supernatant mL | FV mL | FVII mL | PC mL | solution mL | concentration mg/dL |
| L1 | 3.0 | 3.0 | 0.0 | 0.0 | 6.0 | 0.0 | 330.5 |
| L2 | 3.7 | 2.1 | 0.0 | 0.0 | 5.7 | 0.0 | 351.0 |
| L3 | 3.0 | 2.5 | 0.0 | 0.0 | 8.0 | 0.0 | 481.5 |
| L4 | 2.8 | 1.7 | 0.0 | 0.0 | 7.5 | 0.0 | 566.5 |
| L5 | 3.5 | 1.2 | 7.5 | 0.0 | 0.0 | 0.0 | 233.5 |
| L6 | 5.5 | 2.3 | 0.0 | 0.0 | 3.8 | 0.0 | 545.5 |
| L7 | 6.3 | 1.2 | 0.0 | 0.0 | 4.5 | 0.0 | 967.5 |
| L8 | 4.3 | 0.9 | 6.8 | 0.0 | 0.0 | 0.0 | 199.0 |
| L9 | 3.0 | 2.7 | 0.0 | 6.3 | 0.0 | 0.0 | 369.5 |
| L10 | 4.5 | 1.6 | 6.0 | 0.0 | 0.0 | 0.0 | 432.5 |
| L11 | 11.1 | 0.9 | 0.0 | 0.0 | 0.0 | 0.0 | 731.0 |
| L12 | 6.5 | 0.7 | 0.0 | 5.0 | 0.0 | 0.0 | 1006.6 |
| L13 | 12.0 | 0.0 | 0.0 | 0.0 | 0.0 | 0.0 | 237.5 |

TABLE 5

Composition Of The Nonlipemic Samples

| Sample No. | Native sample amount mL | Lipid-containing supernatant mL | Plasma with a deficiency of FV mL | Plasma with a deficiency of FVII mL | Plasma with a deficiency of PC mL | Heparin solution mL | Final triglyceride concentration mg/dL |
|---|---|---|---|---|---|---|---|
| NL1 | 3.0 | — | 0.0 | 0.0 | 9.0 | 0.0 | 91.0 |
| NL2 | 4.0 | — | 0.0 | 0.0 | 8.0 | 0.0 | 95.5 |
| NL3 | 4.0 | — | 0.0 | 0.0 | 8.0 | 0.0 | 103.0 |
| NL4 | 4.0 | — | 0.0 | 0.0 | 8.0 | 0.0 | 87.5 |
| NL5 | 7.0 | — | 5.0 | 0.0 | 0.0 | 0.0 | 62.5 |
| NL6 | 11.5 | — | 0.0 | 0.0 | 0.0 | 0.6 | 53.8 |
| NL7 | 6.0 | — | 0.0 | 0.0 | 6.0 | 0.0 | 88.0 |
| NL8 | 7.0 | — | 0.0 | 0.0 | 5.0 | 0.0 | 92.0 |
| NL9 | 6.0 | — | 6.0 | 0.0 | 0.0 | 0.0 | 105.5 |
| NL10 | 12.0 | — | 0.0 | 0.0 | 0.0 | 0.0 | 83.0 |
| NL11 | 12.0 | — | 0.0 | 0.0 | 0.0 | 0.0 | 120.5 |
| NL12 | 12.0 | — | 0.0 | 0.0 | 0.0 | 0.0 | 73.5 |

2b) Determination of the Lipid Interference in a Method for Determining Protein C Using the Berichrom Protein C Assay In the assay mix, a plasma sample is incubated with a snake venom activator, resulting in the activation of protein C. Furthermore, a chromogenic peptide substrate which is cleaved by activated protein C is added. This reaction achieves an increase in absorbance that is measured at 405 nm. The increase in absorbance is converted to the protein C result (% of the norm) on the basis of a calibration curve. In the example described here, the protein C assay was automatically processed on the Sysmex CS-5100 analyzer (Siemens Healthcare, Marburg, Germany).

From all of the samples prepared under 2a), a subamount was used for the measurement of protein C (assay result 1). A second subamount of each of the samples prepared under 2a) was centrifuged at 133 000×g for 1 hour, and the lipid-depleted phase was used as sample for the protein C measurement (assay result 2). If the centrifugation has no influence, the lipid-depleted phase of the centrifuged aliquot should contain the same analyte amount as the noncentrifuged sample. The two assay results (% of the norm) of each sample were compared with one another, and the relative difference in % was calculated: 100×(assay result 1−assay result 2)/assay result 2.

From the relative differences of the assay results for the nonlipemic samples, the mean was calculated (in this case: −2.4). Since the nonlipemic samples exhibit no interference due to lipemia, this mean difference is attributed to a nonspecific influence factor of the method (e.g., owing to the centrifugation). For the correction of this effect, a corrected difference was ascertained for each sample by subtracting said mean from the relative difference. The corrected difference is a measure of the interference caused by lipids.

Table 6 shows for each sample the assay results 1 and 2, the ascertained relative difference and the corrected difference. The difference values are rounded values.

TABLE 6

Protein C Assay Results And Deviations

| Sample No. | | Triglyceride concentration mg/dL | Noncentrifuged subamount of the sample 1st assay result PC [% of the norm] | Lipid-depleted phase of a centrifuged subamount of the sample 2nd assay result PC [% of the norm] | Relative difference % | Corrected difference % |
|---|---|---|---|---|---|---|
| NL1 | Nonlipemic | 91.0 | 28.7 | 29.3 | −2.0 | 0.3 |
| NL2 | | 95.5 | 30.4 | 31.1 | −2.3 | 0.1 |
| NL3 | | 103.0 | 40.8 | 42.7 | −4.4 | −2.1 |
| NL4 | | 87.5 | 30.6 | 31.3 | −2.2 | 0.1 |
| NL5 | | 62.5 | 76.3 | 76.5 | −0.3 | 2.1 |
| NL6 | | 53.8 | 74.1 | 73.8 | 0.4 | 2.8 |
| NL7 | | 88.0 | 56.1 | 62.1 | −9.6 | −7.2 |
| NL8 | | 92.0 | 53.5 | 54.9 | −2.6 | −0.2 |
| NL9 | | 105.5 | 91.5 | 89.2 | 2.5 | 4.9 |
| NL10 | | 83.0 | 96.2 | 98.3 | −2.1 | 0.2 |
| NL11 | | 120.5 | 110.4 | 114.0 | −3.2 | −0.8 |
| NL12 | | 73.5 | 113.9 | 116.7 | −2.4 | −0.1 |
| | | | | Mean: | −2.4 | |
| L1 | Lipemic | 330.5 | 48.7 | 50.9 | −4.2 | −1.9 |
| L2 | | 351.0 | 44.7 | 46.4 | −3.7 | −1.3 |
| L3 | | 481.5 | 50.4 | 52.1 | −3.3 | −0.9 |
| L4 | | 566.5 | 39.5 | 43.1 | −8.4 | −6.0 |
| L5 | | 233.5 | 81.3 | 85.3 | −4.7 | −2.3 |
| L6 | | 545.5 | 96.7 | 99.3 | −2.6 | −0.2 |
| L7 | | 967.5 | 62.7 | 75.4 | −16.8 | −14.4 |
| L8 | | 199.0 | 83.5 | 85.7 | −2.5 | −0.2 |
| L9 | | 369.5 | 94.1 | 97.3 | −3.2 | −0.9 |
| L10 | | 432.5 | 83.0 | 87.1 | −4.7 | −2.3 |
| L11 | | 731.0 | 100.3 | 109.9 | −8.8 | −6.4 |
| L12 | | 1006.6 | 97.8 | 106.5 | −8.2 | −5.8 |
| L13 | | 237.5 | 105.5 | 110.3 | −4.4 | −2.0 |

Figure 2:
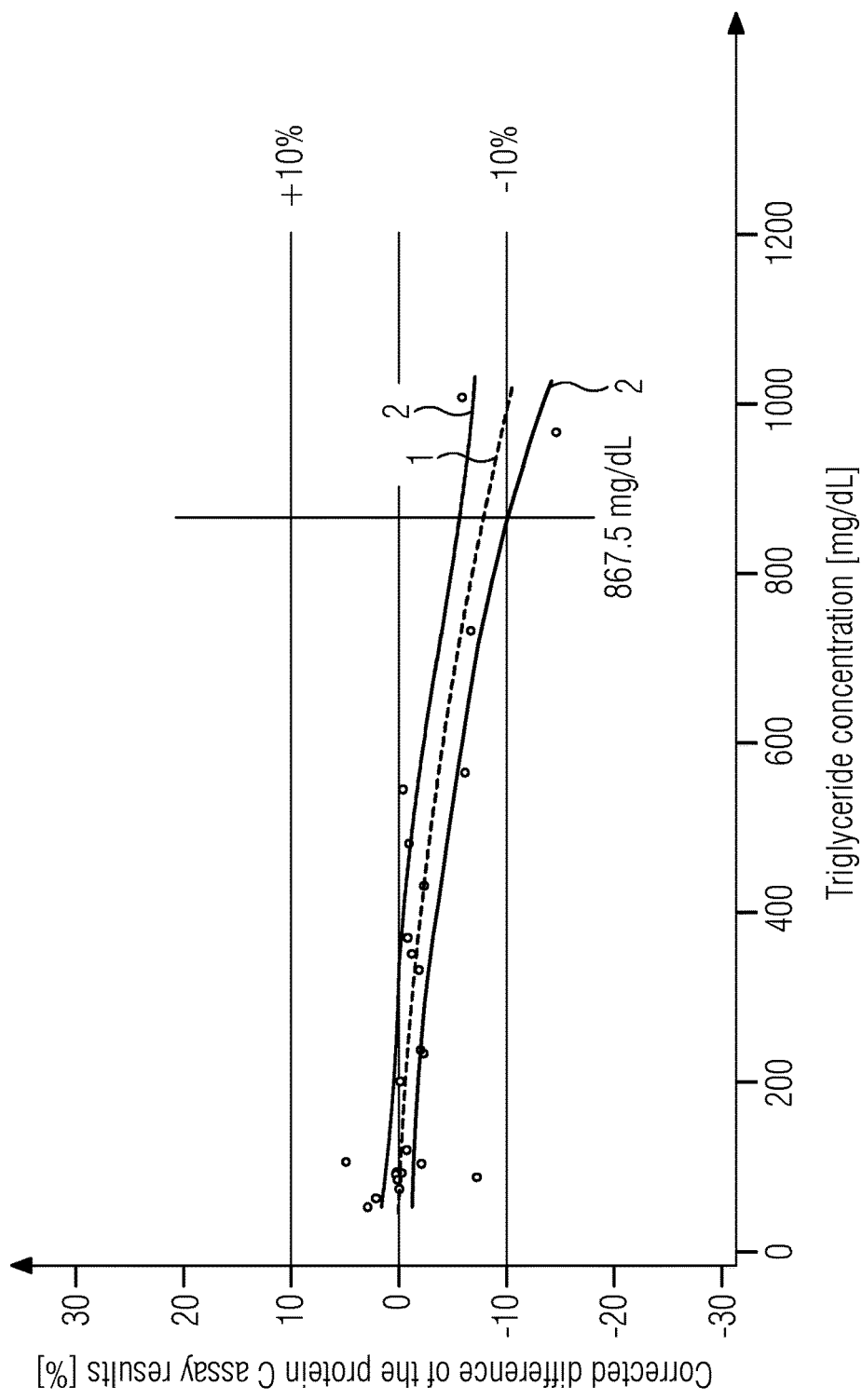
FIG. 2—Determination of the lipid interference in a method for determining protein C.

The corrected difference, i.e., the deviation of the assay results of the noncentrifuged samples from the assay results of the centrifuged samples (decreased by the mean of the difference of the nonlipemic samples), was plotted against the triglyceride concentration of the noncentrifuged samples (FIG. 2, line 1). A polynomial fitting method was applied and the associated confidence interval calculated (FIG. 2, lines 2). The point of intersection of the limit of the confidence interval with the criterion of 10% relative deviation identifies the triglyceride concentration from which a lipid interference is to be expected in the tested protein C assay method (867.5 mg/dL).

The invention claimed is:

1. A method for preparing a lipemic plasma or serum sample, the method comprising the steps:
    (a) centrifuging a lipid-containing plasma or serum sample in order to separate a lipid-containing supernatant from a lipid-depleted phase;
    (b) removing the lipid-containing supernatant and
    (c) mixing the lipid-containing supernatant with a plasma or serum sample.

2. The method as claimed in claim 1, wherein a first subamount of a lipid-containing plasma or serum sample is centrifuged in step (a) and the lipid-containing supernatant is then removed in step (b), and the lipid-containing supernatant is then mixed with a second subamount of the same lipid-containing plasma or serum sample in step (c).

3. The method as claimed in claim 1, wherein the removed lipid-containing supernatant is mixed with a subamount of the lipid-depleted phase.

4. The method as claimed in claim 1, wherein the lipid-containing plasma or serum sample is centrifuged in step (a) for at least 10 minutes at at least 2000×g.

5. A method for establishing a lipid interference in a method for quantitatively determining an amount or an activity of an analyte in a plasma or serum sample, the method for establishing a lipid interference comprising the steps:
    (a) providing a first assay mix by mixing at least one analyte-specific detection reagent with a nonlipemic plasma or serum sample having an analyte concentration or activity and measuring a first assay result;
    (b) providing a second assay mix by mixing the same at least one analyte-specific detection reagent with a lipemic plasma or serum sample having the same analyte concentration or activity and measuring a second assay result;
    (c) establishing a difference between the first and second assay result; and
    (d) establishing a lipid interference when the difference between the first and second assay result exceeds a predetermined tolerance limit;
    wherein the lipemic plasma or serum sample has been prepared using a method as claimed in claim 1.

6. The method as claimed in claim 5, wherein the nonlipemic plasma or serum sample has been prepared using a method comprising the following steps:
    (a) centrifuging a lipid-containing plasma or serum sample and isolating the lipid-depleted phase from the lipid-containing supernatant.

7. The method as claimed in claim 5, wherein the lipemic plasma or serum sample and the nonlipemic plasma or serum sample have been prepared from the same lipid-containing plasma or serum sample as starting material.

8. The method as claimed in claim 5, wherein the nonlipemic and the lipemic plasma or serum sample have in each case an analyte concentration or activity that is reduced or elevated with respect to a norm.

9. A method for establishing a lipid interference in a method for quantitatively determining an amount or an activity of an analyte in a plasma or serum sample, the method for establishing a lipid interference comprising the steps:
    (a) providing a first assay mix by mixing at least one analyte-specific detection reagent with a first subamount of a nonlipemic plasma or serum sample and measuring a first assay result;
    (b) providing a second assay mix by mixing the same at least one analyte-specific detection reagent with a lipid-depleted phase of a second subamount of the same nonlipemic plasma or serum sample, which had previously been centrifuged at at least 2000 g for at least 10 minutes, and measuring a second assay result; and
    (c) establishing a first difference between the first and second assay result; and
    (d) providing a third assay mix by mixing the same at least one analyte-specific detection reagent with a first subamount of a lipemic plasma or serum sample and measuring a third assay result;
    (e) providing a fourth assay mix by mixing the same at least one analyte-specific detection reagent with a lipid-depleted phase of a second subamount of the same lipemic plasma or serum sample, which had previously been centrifuged at at least 2000 g for at least 10 minutes, and measuring a fourth assay result; and
    (f) establishing a second difference between the third and fourth assay result; and
    (g) establishing a lipid interference when a deviation between the first and second difference exceeds a predetermined tolerance limit,
    wherein the lipemic plasma or serum sample has been prepared using a method as claimed in claim 1.

* * * * *